US012728123B2

(12) United States Patent
Svandal et al.

(10) Patent No.: US 12,728,123 B2
(45) **Date of Patent: *Sep. 8, 2026**

(54) PRODUCT

(71) Applicant: Sesh Products Inc., Vancouver (CA)

(72) Inventors: Frank Svandal, Gothenburg (SE); Per Gunnar Nilsson, Malmoe (SE); Robert Ericsson, Helsingborg (SE)

(73) Assignee: Sesh Products Inc., Vancouver (CA)

( * ) Notice: Subject to any disclaimer, the term of this patent is extended or adjusted under 35 U.S.C. 154(b) by 573 days.

This patent is subject to a terminal disclaimer.

(21) Appl. No.: 18/108,135

(22) Filed: Feb. 10, 2023

(65) Prior Publication Data

US 2023/0190729 A1 Jun. 22, 2023

Related U.S. Application Data

(63) Continuation of application No. 13/849,688, filed on Mar. 25, 2013, now Pat. No. 11,590,121.

(60) Provisional application No. 61/615,705, filed on Mar. 26, 2012.

(30) Foreign Application Priority Data

Mar. 26, 2012 (SE) .................................... 1250293-6

(51) Int. Cl.

| | |
|---|---|
| ***A61K 31/465*** | (2006.01) |
| ***A23G 3/48*** | (2006.01) |
| ***A24B 15/16*** | (2020.01) |
| ***A61K 9/00*** | (2006.01) |
| ***A61K 9/14*** | (2006.01) |
| ***A61K 9/68*** | (2006.01) |

(52) U.S. Cl.

CPC .............. *A61K 31/465* (2013.01); *A23G 3/48* (2013.01); *A24B 15/16* (2013.01); *A61K 9/0058* (2013.01); *A61K 9/006* (2013.01); *A61K 9/009* (2013.01); *A61K 9/146* (2013.01)

(58) Field of Classification Search

CPC .... A61K 31/465; A61K 9/0058; A61K 9/006; A61K 9/009; A61K 9/146; A23G 3/48; A24B 15/16

See application file for complete search history.

(56) References Cited

U.S. PATENT DOCUMENTS

2005/0038007 A1* 2/2005 Curatolo .................. A61P 9/10 514/460
2009/0293895 A1* 12/2009 Axelsson ................ A61P 25/34 131/352

FOREIGN PATENT DOCUMENTS

WO WO-2010145653 A1 * 12/2010 .............. A61P 25/34

* cited by examiner

*Primary Examiner* — Jianfeng Song
(74) *Attorney, Agent, or Firm* — Stephen J. Weyer, Esq.; Stites & Harbison, PLLC

(57) ABSTRACT

A nicotine oral delivery product contains a powder enclosed in a water insoluble pouch, wherein the pouch is permeable for saliva and therein dissolved parts of the powder, wherein the powder comprises at least (a) nicotine selected from the group consisting of tobacco, nicotine salts, nicotine base, stabilized nicotine, and mixtures thereof corresponding to 0.1 to 20 mg nicotine in the form of nicotine base and (b) a chewing gum composition. A method is provided for producing the nicotine oral delivery product.

21 Claims, No Drawings

PRODUCT

CROSS REFERENCE TO RELATED APPLICATION

This application is a continuation of U.S. Pat. No. 11,590,121 granted on Feb. 28, 2023 on U.S. patent application Ser. No. 13/849,688, filed Mar. 25, 2013, and claiming priority to U.S. provisional patent application 61/615,705 file Mar. 26, 2012, all herein incorporated by reference.

FIELD OF INVENTION

The invention relates to a nicotine oral delivery product containing a powder enclosed in a water insoluble pouch, wherein said pouch is permeable for saliva and therein dissolved parts of the powder, wherein said powder comprising at least a) nicotine selected from the group consisting of tobacco, nicotine salts, nicotine base, stabilized nicotine, and mixtures thereof corresponding to 0.1 to 20 mg nicotine in the form of nicotine base and b) a chewing gum composition and a method of producing said nicotine oral delivery product.

BACKGROUND OF THE INVENTION

Smoking articles (e. g. cigarettes and cigars) are made from tobacco. The administration of nicotine from tobacco by smoking may provide satisfaction. Smoking is however associated with health hazards which are not necessarily related to the administration of nicotine itself. Important risk factors are substances which are formed or released during the combustion of tobacco, such as carcinogenic nitrosamines, carbon monoxide and tar products. Nicotine is a strongly addictive substance and it is generally accepted that the difficulty to quit smoking results from dependency of nicotine.

As smoking of tobacco has severe health hazards it is desirable to have alternative, less harmful, means of administering nicotine in a pleasurable manner as an alternative to smoking, or to facilitate reduction of or cessation from smoking. Worldwide, a number of smokeless tobacco products and other nicotine containing products are available. Smokeless tobacco administration forms include snus, snuff, dissolvable tobacco, tobacco chewing gum and various types of chewing tobacco. Non-tobacco nicotine administration forms used for nicotine replacement therapy (NRT), a process for smoking cessation, include chewing gum, lozenge, spray and oral pouch.

The rate of the nicotine release and the dose of nicotine are important characteristics of a nicotine product. When smoking a cigarette, nicotine is almost immediately absorbed and quickly reaches the brain. The quick uptake gives the smoker rapid satisfaction. Therefore, for smoking replacement, an initial rapid absorption of a sufficiently high dose of nicotine is desirable. Further, a sustained absorption of nicotine is also desirable if it maintains the blood plasma level of nicotine high enough to relief craving over a period of time. It is therefore desirable to provide non-smoking nicotine products with an initial rapid release of a sufficiently high dose of nicotine followed by a sustained release of nicotine over a period of time. In particular, it is desirable to provide non-smoking nicotine products where the user himself can control the nicotine release.

Snus or snuff is a tobacco mixture from which the user forms a portion and places it in the oral cavity, usually under the upper or lower lip. Alternatively, the tobacco mixture is already portioned into pouches. The use of snus normally results in nicotine blood plasma levels with a rather high steady state nicotine concentration. It does however not provide the rapid nicotine peak levels obtained from smoking as nicotine is released rather slowly from snus. The user of snus has rather limited possibilities to boost the nicotine release if desired.

Similarly, the users of dissolvable tobacco, or NRT lozenges, spray and oral pouches have rather limited possibilities to control the nicotine release rate from the products.

Certain nicotine products are intended to be chewed by the user. These include chewing tobacco, tobacco chewing gum and nicotine non-tobacco chewing gum.

Chewing tobacco is made from tobacco that is not milled or grounded. The tobacco has to be mechanically crushed with the teeth to release the nicotine. Different chewing tobacco formulations are available, such as loose leaf tobacco, plug tobacco, twist tobacco and tobacco bits. A user of chewing tobacco chews the product until it produces a satisfactory nicotine effect. The product is then parked, for example, in between the cheek and gums. When the user desires additional nicotine it is chewed again and is thereafter once again parked. These steps are repeated until the chewing tobacco is depleted of nicotine or the craving dissipates. The use of chewing tobacco results in an excessive excretion of saliva which is spitted or swallowed. Chewing tobacco is therefore often considered to be somewhat disgusting and may not be the first choice for smokers who want to replace the smoking habit with an alternative nicotine delivery system.

Nicotine non-tobacco chewing gums are used in NRT. An example is Nicorette® chewing gum which consists of a nicotine complex with an insoluble cation exchanger (polacrilex) that is dispersed in a chewing gum composition. Nicotine non-tobacco chewing gums are used very much in the same way as chewing tobacco, i.e. they are chewed until they produce a satisfactory nicotine effect and are then parked. Nicotine non-tobacco chewing gums generally suffer from a slow nicotine release from the product. It may take about 5 minutes of chewing before the effect of nicotine is first noticed. This does not give the user the same satisfaction as smoking, with an initial fast absorption of nicotine.

Tobacco chewing gums, i.e. chewing gums containing finely powdered tobacco, are available in certain markets. As the tobacco is embedded into a compact chewing gum mass, these products most likely also suffer from a slow initial nicotine release.

It is desirable to provide an improved non-smoking nicotine product as an alternative to smoking articles. The product should be attractive to the consumer. The nicotine release should be user controlled. The product should be able to provide an initial rapid and sufficiently high dose of nicotine followed by a sustained release of nicotine. This will give a satisfaction from the nicotine similar to smoking, followed by a period of craving relief.

SUMMARY OF THE INVENTION

In a first aspect the invention relates to a nicotine oral delivery product containing a powder enclosed in a water insoluble pouch, wherein said pouch is permeable for saliva and therein dissolved parts of the powder, wherein said powder comprising at least a) nicotine selected from the group consisting of tobacco, nicotine salts, nicotine base, stabilized nicotine, and mixtures thereof corresponding to 0.1 to 20 mg nicotine in the form of nicotine base and b) a chewing gum composition.

By the invented new nicotine oral delivery product the above identified problems with the existing products are solved and thus an improved product obtained.

In a second aspect the invention relates to a method of making a product comprising the steps of a) providing a powder comprising at least nicotine selected from the group consisting of tobacco, nicotine salts, nicotine base, stabilized nicotine, and mixtures thereof corresponding to 0.1 to 20 mg nicotine in the form of nicotine base, and a chewing gum composition,
b) enclosing said powder into a pouch and
c) obtaining a product as defined above as well as under the description of the invention.

The user of the invented product can control the release of nicotine from the product, as it is chewable. If the user initially gently chew the nicotine chewing pouch for a short period of time and then park it, the product will give an initial rapid and sufficiently high dose of nicotine followed by a sustained release of nicotine. The user can gently chew the product again when an additional nicotine boost is required. Thus the user can control the release of nicotine from the product.

After a short period of chewing on a nicotine chewing pouch, the chewing gum composition in the pouch has transformed into a coherent chewing gum mass. In this process, the other components of the powder become fully or partially embedded into the chewing gum mass.

DETAILED DESCRIPTION OF THE INVENTION

Definitions

The term "stabilized nicotine" is intended to mean nicotine bound to, adsorbed to, absorbed into, enclosed into or forming a complex or any other non-covalent binding with another component or components. A number of stabilized nicotine combinations are well known in previous art.

The term "chewing gum composition" is intended to mean all chewing gum compositions which transforms into a chewing gum mass when chewed. The term "pH adjusting agent" is intended to mean one or more substances which adjust and control the pH of an aqueous liquid, such as saliva, when the product containing the pH adjusting agent is dissolved or dispersed in said aqueous liquid.

The term "encapsulated pH adjusting agent" is intended to mean a pH adjusting agent which has been encapsulated or embedded into another component, such as a polymer, in order to physically separate it from nicotine selected from the group consisting of tobacco, nicotine salts, nicotine base, stabilized nicotine, and mixtures thereof in the product.

The term "soluble in saliva" is intended to mean a component which has a solubility in saliva which adequate for its intended use.

The term "pharmaceutically acceptable" is intended to mean non-toxic compounds or materials that are biocompatible and physiologically acceptable, and do not decrease the effectiveness of the biological activity of the active ingredient, i.e. nicotine. Such pharmaceutically acceptable compounds or materials are well-known in the art (see for example Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

Product

The invention relates to a nicotine oral delivery product containing a powder enclosed in a water insoluble pouch, wherein said pouch is permeable for saliva and therein dissolved parts of the powder, wherein said powder comprising at least a) nicotine selected from the group consisting of tobacco, nicotine salts, nicotine base, stabilized nicotine, and mixtures thereof corresponding to 0.1 to 20 mg nicotine in the form of nicotine base and
b) a chewing gum composition.

Nicotine selected from the group consisting of tobacco, nicotine salts, nicotine base, stabilized nicotine, and mixtures thereof includes tobacco.

Tobacco includes any part, e.g. leaves, flowers, stems, of any member of the genus *Nicotiana*, and reconstituted material thereof.

In one form nicotine selected from the group consisting of tobacco, nicotine salts, nicotine base, stabilized nicotine, and mixtures thereof may be a nicotine salt. The nicotine salt shall be soluble in saliva. Examples of nicotine salts include nicotine hydrochloride, nicotine dihydrochloride, nicotine monotartrate, nicotine bitartrate, nicotine bitartrate dihydrate, nicotine sulphate, nicotine zinc chloride monohydrate, nicotine salicylate, and mixtures thereof.

In another form nicotine selected from the group consisting of tobacco, nicotine salts, nicotine base, stabilized nicotine, and mixtures thereof may be stabilized nicotine, which means that it is bound to, adsorbed to, absorbed into, enclosed into or forming a complex or any other non-covalent binding with another component or components. A number of stabilized nicotine combinations are well known in previous art. Examples include nicotine bound to a cation exchange resin such as Amberlite IRP 64 (Amberlite IRP 64 is derived from a copolymer of methacrylic acid and divinylbenzene), zeolites, cellulose and cellulose derivatives, as well as starch microspheres and beta-cyclodextrin inclusion complexes.

The amount of nicotine selected from the group consisting of tobacco, nicotine salts, nicotine base, stabilized nicotine, and mixtures thereof in the product may be from 0.1 mg to 20 mg of nicotine, calculated as nicotine base ($C_{10}H_{14}N_2$, CAS no. 54-11-5), preferable from 0.1 to 10 mg of nicotine such as 0.5, 1.0, 1.5, 2.0, 2.5, 3.0, 3.5, 4.0, 4.5, 5.0, 5.5, 6.0, 6.5, 7.0, 7.5, 8.0, 8.5, 9.0 or 9.5 mg of nicotine.

The chewing gum composition according to the invention may be a powdered chewing gum composition, and such compositions are commercially available for other applications than described here. Chewing gum tablets can be manufactured by compressing a powdered chewing gum composition in a tabletting machine. Chewing gums can also be manufactured from powdered chewing gum compositions by coating cores in conventional panning equipment. Examples of suitable powdered chewing gum compositions are PG NEW NUTRA TA from Gum Base Co., Italy and Chewycoat powder SF from Alsiano, Denmark.

The chewing gum composition according to the disclosed invention contains up to 100 percent of a chewing gum base, but the chewing gum composition may also contain additives. The chewing gum base may be water-insoluble and non-digestible, i.e. it is not dissolved during chewing. Chewing gum bases normally comprise hydrophobic and elastic substances that enable it to be chewed for a long time without experiencing substantial changes. The chewing gum base may be of any type as long as the chewing gum composition transforms into a chewing gum mass then it is chewed.

Additives are often added to give improved product and processing properties to the chewing gum composition. Such additives include texture regulating agents, flow-improving agents, anti-caking agents, fillers and the like. Examples of such additives are magnesium stearate, silicon dioxide, talc, maltitol and isomalt.

Optionally, additives can be added to the nicotine oral delivery product to give the product improved properties when it comes to experience and effect of the product on the user. These additives can be added to the powder or be incorporated into the chewing gum composition or into nicotine selected from the group consisting of tobacco, nicotine salts, nicotine base, stabilized nicotine, and mixtures thereof, or any combination thereof. The type of additives, the amount of additives and the distribution of additives in the product are chosen depending on the desired properties of the final product. Examples of such additives can be selected from the group consisting of pH adjusting agents, sweeteners, flavors, fillers, and mixtures thereof. They will for example provide a suitable pH when the product is used, an attractive taste, or a suitable size of the product.

Absorption of nicotine from the oral cavity, i.e. transmucosal uptake, to the systemic circulation is dependent on the local pH of the saliva. The local pH is the pH inside and in close proximity to the product. Nicotine will predominantly be absorbed through the mucosa in the nonprotonated form. Therefore, a local pH which results in a high fraction of the nonprotonated nicotine is desirable. The pKa of nicotine is about 7.8 which mean, for example, that at a pH of about 8.8 approximately 90% of the nicotine is in the nonprotonated form. By pH adjusting, the local pH of the saliva can be increased and therefore the absorption of nicotine is increased compared to if no pH adjustment was done.

A pH adjusting agent shall be a pharmaceutically acceptable and may provide a pH of 6 or above when the powder in the product is dissolved or dispersed in purified water. Examples of such pH adjusting agents are carbonates including monocarbonate, bicarbonate and sesquicarbonate, acetates, glycinates, gluconates, borates, glycerophosphates or citrates of alkaline metals or ammonium, phosphate systems including monohydrogenphosphate, dihydrogenphosphate and trihydrogenphosphate, metal hydroxides, such as sodium hydroxide and potassium hydroxide, and mixtures thereof. Preferred pH adjusting agents are sodium bicarbonate and sodium carbonate, and mixtures thereof.

In some embodiments it might be that the nicotine selected from the group consisting of tobacco, nicotine salts, nicotine base, stabilized nicotine, and mixtures thereof and the pH adjusting agent need to be separated from each other in the product during storage. An example is when nicotine selected from the group consisting of tobacco, nicotine salts, nicotine base, stabilized nicotine, and mixtures thereof is an acidic nicotine salt. A high pH can then have a negative effect on the stability of an otherwise stable nicotine component. In these cases the pH adjusting agent may be encapsulated or embedded for example with a polymer before mixing it with the other components. Such encapsulating or embedding will protect the nicotine component from the alkaline components in the pH adjusting agent. The nicotine component and the pH adjusting agent will mix directly only, during use, when the saliva is dissolving and releasing the components into the oral cavity.

Examples of sweeteners include mono- di- tri- and polysaccharides, polyols such as mannitol and maltitol, natural and synthetic sweeteners such as sucrose, glucose, dextrose, maltose, fructose, saccharin, aspartame, acesulfame, sucralose, saccharin and cyclamates, and mixtures thereof.

Examples of flavors include bergamot, eucalyptus, orange, mandarin, citrus, lemon, peppermint, mint, menthol, liquorice, wintergreen, tobacco, coffee, vanilla, lime, apple, peach, and mixtures thereof.

Examples of fillers include polysaccharides, polyols, sugars, natural fibers, microcrystalline cellulose, cellulose and cellulose derivatives, and mixtures thereof. A filler may also have a secondary function, for example as sweetener.

Optionally, the powder mixture, or part of the powder mixture, can be granulated. The granulation increases the particle size of the powder which can for example decrease the dustiness of the powder or improve the powder flow. Examples of suitable granulating agents are polyvinylpyrrolidone (such as Kollidon 25) or anionic copolymers based on methacrylic acid and methyl methacrylate (such as Eudragit L100).

The product may comprise from 50 to 2000 mg of said powder, such as 50 to 1000 mg, such as 200 to 600 mg, such as 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900 or 1950 mg.

The powder is filled into pouches and is maintained in the pouch by a sealing. An ideal pouch shall have the following characteristics: it shall be chemically and physically stable, be pharmaceutically acceptable, be insoluble in water, be easy to fill with powder and seal and it shall provide a semi-permeable membrane layer which prevent the powder from leaving the bag but permit saliva and therein dissolved components from the powder in the pouch, such as nicotine, to freely pass through said pouch.

The pouch material may be of any suitable material e.g. woven or non-woven fabric (e.g. cotton, fleece etc.), heat sealable non-woven cellulose or other polymeric material such as synthetic, semi-synthetic or natural polymeric material. An example of suitable pouch material is paper made of pulp and a small amount of wet strength agent.

The pouch is placed in the oral cavity by the user. Saliva enters into the pouch, and nicotine and other components which are soluble in saliva start to dissolve and are transported with the saliva out of the pouch into the oral cavity where the nicotine is absorbed. Depending on the required nicotine dose, the user can alternatively chew the pouch gently, or park the pouch in a suitable place in the oral cavity. When more nicotine is required, the user gently chews the pouch for a short time period resulting in a boost of nicotine. When the user is satisfied with the spontaneous nicotine release from the pouch, without chewing, the pouch can be parked for example in between the cheek and the gums.

After a short time of chewing, the chewing gum composition in the pouch has transformed into a chewing gum mass with all or most of the other powder components incorporated into the chewing gum mass. Contrary to conventional nicotine chewing gums, the chewing gum mass is formed in situ in the oral cavity by the chewing action of the user. When the chewing gum mass has formed, the product will behave similar to a nicotine chewing gum product with respect to the nicotine release.

If the chewing causes a rupture of the pouch, the user will not get any, or a very limited amount of, powdered material in the mouth as most of the powdered content in the pouch has been incorporated into a chewing gum mass. After use, the product is discarded.

The product can be differently designed depending on the required delivery of nicotine. In one embodiment, the nicotine selected from the group consisting of tobacco, nicotine salts, nicotine base, stabilized nicotine, and mixtures thereof is initially, before use, not embedded into the chewing gum composition, but the chewing gum composition comprises of particles being free from nicotine selected from the group consisting of tobacco, nicotine salts, nicotine base, stabilized nicotine, and mixtures thereof. In this embodiment, the release of nicotine is initially only marginally influenced by the presence of the chewing gum composition. When chewed, the nicotine can initially be very rapidly released to the user. In contrast, if nicotine selected from the group consisting of tobacco, nicotine salts, nicotine base, stabilized nicotine, and mixtures thereof is initially embedded into the chewing gum composition, a somewhat slower initial nicotine release is obtained (cf. nicotine chewing gums).

Method

The invention also relates to a method to manufacture the oral delivery nicotine product according to the disclosed invention.

When the components are mixed to form the powder, it is possible to employ a variety of compositions and mixing variations. Products may be designed with respect to the nicotine level and nicotine release rate, or other features.

The manufacture comprise the steps of providing a powder consisting of nicotine selected from the group consisting of tobacco, nicotine salts, nicotine base, stabilized nicotine, and mixtures thereof, a chewing gum composition and optionally additives, and filling said powder into pouches which are sealed.

The mixing may be performed in a conventional blender. One or more sieving steps may be advantageous to improve the blending homogeneity. Additional manufacturing steps may be needed for example if any of the components is a liquid. Nicotine base is liquid. Typically, several flavors are liquids or liquid solutions. In that case, for example, an absorption/adsorption step or a drying step may be needed.

The powder, or part of the powder (for example an additive mixture), may be granulated. A granulation increases the particle size of the powder which can decrease the dustiness of the powder or improve the powder flow.

In one embodiment, a pH adjusting agent may be encapsulated or embedded with for example a polymer before mixing it with the other components. This can be performed by adding a polymer solution to the pH adjusting agent and evaporating the solvent to form a powder consisting of the pH adjusting agent encapsulated or embedded with a polymer.

By such a simple and controlled manufacturing process, it is possible to obtain an attractive and effective product.

The following examples are provided to illustrate the disclosed invention, but should not be interpreted as limiting the scope thereof.

EXAMPLES

Example 1

Chewable nicotine pouches containing different proportions between tobacco and chewing gum composition, as well as different fill weights of powder, have been manufactured.

Powdered tobacco with an average particle size of approximately 300 μm (according to sieve analysis) was used. The tobacco contains approximately 6% nicotine (calculated as nicotine base).

PG NEW NUTRA TA from Gum Base Co., Italy was used as chewing gum composition.

Tobacco and PG NEW NUTRA TA were sieved and mixed to form a powder mixture. Three powder mixtures with different proportions between the two components were manufactured (batches 1A, 1B and 1C). The batch sizes were 50 g.

The powders were filled into pouches which were sealed. The pouches were manufactured from paper made of pulp and a small amount of wet strength agent. Different amounts of powder were filled into the pouches.

pH was determined for pouches from the different batches. A pouch was stirred or shaken in 15 g purified water for at least 30 minutes. Thereafter pH was determined with a conventional pH-meter.

The percent tobacco in the powders and the amounts of the powders filled into pouches are presented in Table 1 below. The content of nicotine (calculated as nicotine base) and the pH are also presented as well as the amounts of the both components in a pouch.

TABLE 1

Properties of batches in Example 1.

| Batch number | 1A1 | 1B1 | 1C1 | 1C2 | 1C3 |
|---|---|---|---|---|---|
| Powder batch number | 1A | 1B | 1C | 1C | 1C |
| Tobacco in powder batch (%) | 3.33 | 20.0 | 33.3 | 33.3 | 33.3 |
| Fill weight powder in pouches (mg) | 50 | 167 | 250 | 500 | 1000 |
| Nicotine (mg/pouch)(*) | 0.1 | 2.0 | 5.0 | 10 | 20 |
| pH | 6.8 | 7.6 | 7.9 | 7.8 | 8.1 |
| Composition of the pouches (mg/pouch) | | | | | |
| Tobacco | 1.7 | 33.4 | 83.3 | 167.7 | 333.3 |
| PG NEW NUTRA TA | 48.3 | 133.6 | 166.7 | 333.3 | 666.7 |

(*)Calculated from the amount of tobacco assuming 6% nicotine

It is seen that the pH is above 6 for all batches.

Pouches were tested by volunteers. A pouch was placed in the mouth, and was gently chewed. Thereafter the pouch was taken out an inspected. For all batches, a solid chewing gum mass had formed from the powder in the pouch.

Example 2

Chewable nicotine pouches containing tobacco, chewing gum composition and a granulated additive mixture have been manufactured.

Powdered tobacco with an average particle size of approximately 300 μm (according to sieve analysis) was used. The tobacco contains approximately 6% nicotine (calculated as the nicotine base).

Chewycoat powder SF from Alsiano was used as chewing gum composition.

A granulated additive mixture was manufactured in the following way: 1040 g maltitol, 300 g sodium bicarbonate and 20.0 g Acesulfame K were sieved and mixed to form a powder mixture. 40.0 g Kollidon 25 (polyvinylpyrrolidone) was dissolved in 60.0 g ethanol to form a granulation liquid. The granulation liquid was slowly added to the powder mixture under stirring. The granulate was allowed to dry. This is additive mixture BT-001.

Tobacco, Chewycoat powder SF and part of the additive mixture BT-001 were mixed. The batch sizes were 100 g and following proportions were used:

TABLE 2

Compositions of the powder batches (weight-%)

| Powder batch number | 2A | 2B | 2C |
|---|---|---|---|
| Tobacco | 12.3 | 18.5 | 24.7 |
| Chewycoat powder SF | 50.0 | 50.0 | 50.0 |
| Additive mixture BT-001 | 37.7 | 31.5 | 25.3 |

The powders were filled into pouches which were sealed. The pouches were manufactured from paper made of pulp and a small amount of wet strength agent. A pouch was filled with approximately 270 mg or 540 mg of powder.

pH was determined for pouches from the different batches. A pouch was stirred or shaken in 15 g purified water for at least 30 minutes. Thereafter pH was determined with a conventional pH-meter.

The fill weight, the content of nicotine (calculated as nicotine base) and the pH for the different batches are presented in Table 3 below. The amounts of the different components in a pouch are also presented.

TABLE 3

Properties of the batches in Example 2.

| Batch number | 2A1 | 2B1 | 2C1 | 2A2 | 2B2 | 2C2 |
|---|---|---|---|---|---|---|
| Powder batch number | 2A | 2B | 2C | 2A | 2B | 2C |
| Fill weight powder in pouches (mg) | 270 | 270 | 270 | 540 | 540 | 540 |
| Nicotine (mg/pouch) (*) | 2 | 3 | 4 | 4 | 6 | 8 |
| pH | 8.1 | 8.1 | 8.0 | 8.2 | 8.1 | 7.9 |
| Composition of the pouches (mg/pouch) | | | | | | |
| Tobacco | 33.3 | 50.0 | 66.7 | 66.7 | 100.0 | 133.4 |
| Chewycoat powder SF | 135.0 | 135.0 | 135.0 | 270.0 | 270.0 | 270.0 |
| Maltitol | 75.5 | 63.2 | 50.7 | 151.0 | 126.4 | 101.4 |
| Sodium bicarbonate | 21.8 | 18.2 | 14.6 | 43.6 | 36.4 | 29.2 |
| Acesulfame K | 1.5 | 1.2 | 1.0 | 3.0 | 2.4 | 2.0 |
| Kollidon 25 | 2.9 | 2.4 | 2.0 | 5.8 | 4.8 | 4.0 |

(*) Calculated from the amount of tobacco assuming 6% nicotine

It is seen that the pH is above 6 for all batches.

Pouches were tested by volunteers. A pouch was placed in the mouth and was gently chewed. Thereafter the pouch was taken out an inspected. For all batches, a solid chewing gum mass had formed from the powder in the pouch.

Example 3

Chewable nicotine pouches containing nicotine polacrilex, chewing gum composition and a granulated additive mixture have been manufactured.

Nicotine polacrilex resin from Cambrex was used. The nicotine is bound to Amberlite IRP64. The powder contains 15% nicotine (calculated as nicotine base).

Chewycoat powder SF from Alsiano was used as chewing gum composition The additive mixture BT-001, described in Example 2, was used.

Nicotine polacrilex, Chewycoat powder SF and additive mixture BT-001 were sieved and mixed. The batch sizes were 100 g and following proportions were used:

TABLE 4

Compositions of the powder batches (weight-%)

| Powder batch number | 3A | 3B | 3C |
|---|---|---|---|
| Nicotine polacrilex | 4.9 | 7.4 | 9.9 |
| Chewycoat powder SF | 50.0 | 50.0 | 50.0 |
| Additive mixture BT-001 | 45.1 | 42.6 | 40.1 |

The powders were filled into pouches which were sealed The pouches were manufactured from paper made of pulp and a small amount of wet strength agent. A pouch is filled with approximately 270 mg or 540 mg of powder.

pH was determined for pouches from the different batches. A pouch was stirred or shaken in 15 g purified water for at least 30 minutes. Thereafter pH was determined with a conventional pH-meter.

The fill weight, the content of nicotine (calculated as nicotine base) and the pH for the different batches are presented in Table 5 below. The amounts of the different components in a pouch are also presented.

TABLE 5

Properties of the batches in Example 3.

| Batch number | 3A1 | 3B1 | 3C1 | 3A2 | 3B2 | 3B2 |
|---|---|---|---|---|---|---|
| Powder batch number | 3A | 3B | 3C | 3A | 3B | 3C |
| Fill weight powder in pouches (mg) | 270 | 270 | 270 | 540 | 540 | 540 |
| Nicotine (mg/pouch) (*) | 2 | 3 | 4 | 4 | 6 | 8 |
| pH | 7.5 | 7.3 | 7.2 | 7.5 | 7.3 | 7.3 |
| Composition of the pouches (mg/pouch) | | | | | | |
| Nicotine polacrilex | 13.3 | 20.0 | 26.7 | 26.6 | 40.0 | 53.4 |
| Chewycoat powder SF | 135.0 | 135.0 | 135.0 | 270.0 | 270.0 | 270.0 |
| Maltitol | 90.4 | 85.4 | 80.5 | 180.8 | 170.8 | 161.0 |
| Sodium bicarbonate | 26.1 | 24.6 | 23.2 | 52.2 | 49.2 | 46.4 |
| Acesulfame K | 1.7 | 1.6 | 1.5 | 3.4 | 3.2 | 3.0 |
| Kollidon 25 | 3.5 | 3.3 | 3.1 | 7.0 | 6.6 | 6.2 |

(*) Calculated from the amount of Nicotine polacrilex assuming 15% nicotine

It is seen that the pH is above 6 for all batches.

Pouches were tested by volunteers. A pouch was placed in the mouth and was gently chewed. Thereafter the pouch was taken out an inspected. For all batches, a solid chewing gum mass formed from the powder in the pouch.

Example 4

Chewable nicotine pouches containing nicotine bitartrate dihydrate, chewing gum composition and different additive mixtures have been manufactured.

Nicotine bitartrate dihydrate from Nicobrand, Londonderry, Northern Ireland was used. The powder contains approximately 31% nicotine (calculated as nicotine base).

Chewycoat powder SF from Alsiano was used as chewing gum composition.

Three powder mixtures have been manufactured (4A, 4B and 4C). The powder mixtures contain different granulated additive mixtures.

The granulated additive mixture BT-003 was used in powder mixture 4A. It was manufactured in the following way: 550 g maltitol, 325 g sodium bicarbonate, 75.0 g sodium carbonate and 20.0 g Acesulfame K were sieved and mixed to form a powder mixture. 30.0 g Kollidon 25 (polyvinylpyrrolidone) was dissolved in 45.0 g ethanol to form a granulation liquid. The granulation liquid was slowly added to the powder mixture under stirring. The granulate was allowed to dry.

"Encapsulated pH adjusting agent 1" was used in powder mixture 4B. It was manufactured in the following way: 495 g sodium bicarbonate and 285 g sodium carbonate were mixed. 60.0 g Eudragit L100 (anionic copolymer based on methacrylic acid and methyl methacrylate) was dissolved in 340 g ethanol. The granulation solution was slowly added to the powder mixture under stirring in a planetary mixer. The moist granulate was sieved and placed on a tray. The powder was dried at ambient conditions over night and was thereafter sieved.

"Encapsulated pH adjusting agent 2" was used in powder mixture 4C. It was manufactured in the same way as "Encapsulated pH adjusting agent 1" with the only difference that other amounts of the pH adjusting agents were used: 345 g sodium bicarbonate and 435 g sodium carbonate.

Chewable nicotine pouches containing nicotine bitartrate dihydrate were manufactured in the following way: Nicotine bitartrate dihydrate, Chewycoat powder SF and the granulated additive mixture were mixed and sieved. The batch sizes were 25 g to 50 g. The powders were filled into pouches which were sealed. The pouches were manufactured from paper made of pulp and a small amount of wet strength agent. Pouches were filled with approximately 200 mg of powder.

pH was determined for the pouches from the different batches. A pouch was stirred or shaken in 15 g purified water for at least 30 minutes. Thereafter pH was determined with a conventional pH-meter.

The content of nicotine (calculated as nicotine base) and the pH for the different batches are presented in Table 6 below. The amounts of the different components in a pouch are also presented.

TABLE 6

Properties of the batches in Example 4.

| Batch number | 4A1 | 4B1 | 4C1 |
|---|---|---|---|
| Powder batch number | 4A | 4B | 4C |
| Nicotine (mg/pouch) (*) | 1 | 3 | 5 |
| pH | 8.6 | 8.4 | 9.4 |
| Composition of the pouches (mg/pouch) | | | |
| Nicotine bitartrate dihydrate | 3.1 | 9.2 | 15.3 |
| Chewycoat powder SF | 131.9 | 162.8 | 156.7 |
| Maltitol | 35.8 | — | — |
| Sodium bicarbonate | 21.1 | 16.5 | 11.5 |
| Sodium carbonate | 4.9 | 9.5 | 14.5 |
| Acesulfame K | 1.3 | — | — |
| Kollidon 25 | 2.0 | — | — |
| Eudragit L100 | | 2.0 | 2.0 |

(*) Calculated from Nicotine bitartrate dihydrate assuming 31% nicotine

It is seen that the pH is above 6 for all batches.

Pouches were tested by volunteers. A pouch was placed in the mouth and was gently chewed. Thereafter the pouch was taken out an inspected. For all batches, a solid chewing gum mass had formed from the powder in the pouch.

Example 5

The manufacture of batches 2B1, 3B1 and 4B1, described in Examples 2-4 above, has been repeated with the only difference that PG NEW NUTRA TA from Gum Base Co., Italy was used as chewing gum composition instead of Chewycoat powder SF from Alsiano.

pH was determined for pouches from the different batches. A pouch was stirred or shaken in 15 g purified water for at least 30 minutes. Thereafter pH was determined with a conventional pH-meter.

The following results were obtained:

TABLE 7 pH for the pouches in Example 5

| Batch number | 5A1 | 5B1 | 5C1 |
|---|---|---|---|
| Corresponding batch number with Chewycoat powder SF | 2B1 | 3B1 | 4B1 |
| pH | 7.8 | 8.7 | 8.7 |

It is seen that the pH is above 6 for all batches.

Pouches were tested by volunteers. A pouch was placed in the mouth and was gently chewed. Thereafter the pouch was taken out an inspected. For all batches, a solid chewing gum mass had formed from the powder in the pouch.

Example 6

Chewable nicotine pouches with the same amount of tobacco but with different amounts of chewing gum composition and additives have been manufactured.

Powdered tobacco with an average particle size of 300 μm (according to sieve analysis) was used. The tobacco contains approximately 6% nicotine (calculated as nicotine base).

Chewycoat powder SF from Alsiano was used as chewing gum composition. The granulated additive mixture BT-001, described in Example 2, was used.

Tobacco, Chewycoat powder SF and additive mixture BT-001 were mixed and sieved to form a powder mixture. The batch sizes were 100 g.

TABLE 8

Composition of the powder batches (weight-%)

| Powder batches | 6A | 6B |
|---|---|---|
| Tobacco | 18.5 | 18.5 |
| Chewycoat powder SF | 30.0 | 70.0 |
| Additive mixture BT-001 | 51.5 | 11.5 |

The powders were filled into pouches which were sealed. The pouches were manufactured from paper made of pulp and a small amount of wet strength agent. The fill weight was 270 mg.

pH was determined for pouches from the different batches. A pouch was stirred or shaken in 15 g purified water for at least 30 minutes. Thereafter pH was determined with a conventional pH-meter.

The content of nicotine (calculated as nicotine base) and the pH for the both batches are presented in Table 9 below. The amounts of the different components in a pouch are also presented.

TABLE 9

Properties of the batches in Example 6.

| Batch number | 6A1 | 6B1 |
|---|---|---|
| Powder batch number | 6A | 6B |
| Nicotine (mg/pouch) (*) | 3 | 3 |
| pH | 8.2 | 8.0 |
| Composition of the pouches (mg/pouch) | | |
| Tobacco | 50.0 | 50.0 |
| Chewycoat powder SF | 81.0 | 189.0 |
| Maltitol | 103.3 | 23.0 |
| Sodium bicarbonate | 29.8 | 6.6 |
| Acesulfame K | 2.0 | 0.4 |
| Kollidon 25 | 4.0 | 0.9 |

(*) Calculated from the amount of tobacco assuming 6% nicotine

It is seen that the pH is above 6 for both batches.

Pouches were tested by volunteers. A pouch was placed in the mouth and was gently chewed. Thereafter the pouch was taken out an inspected. For both batches, a solid chewing gum mass formed from the powder in the pouch.

The invention claimed is:

1. A nicotine oral delivery product containing a powder enclosed in a water insoluble pouch, wherein said pouch is permeable for saliva and therein dissolved parts of the powder, wherein said powder comprising at least a) nicotine selected from the group consisting of tobacco, nicotine salts, nicotine base, stabilized nicotine, and mixtures thereof corresponding to 0.1 to 20 mg nicotine in the form of nicotine base and b) a granulated a chewing gum composition which transforms into a coherent chewing gum mass when chewed, wherein the chewing gum composition contains a hydrophobic, water-insoluble and non-digestible chewing gum base comprising an elastic substance.

2. The product according to claim 1, wherein said nicotine is tobacco or nicotine salt, and mixtures thereof.

3. The product according to claim 2, wherein said nicotine salt is selected from the group consisting of nicotine hydrochloride, nicotine dihydrochloride, nicotine monotartrate, nicotine bitartrate, nicotine bitartrate dihydrate, nicotine sulphate, nicotine zinc chloride monohydrate and nicotine salicylate, and mixtures thereof.

4. The product according to claim 3, wherein said nicotine salt is nicotine bitartrate dihydrate.

5. The product according to claim 1, wherein said nicotine is nicotine base.

6. The product according to claim 1, wherein said nicotine is stabilized nicotine.

7. The product according to claim 1, wherein said product comprises nicotine selected from the group consisting of tobacco, nicotine salts, nicotine base, stabilized nicotine, and mixtures thereof in an amount from 0.1 to 10 mg per product calculated as nicotine in the form of nicotine base.

8. The product according to claim 7, wherein said product comprises nicotine selected from the group consisting of tobacco, nicotine salts, nicotine base, stabilized nicotine, and mixtures thereof in an amount of 0.5, 1.0, 1.5, 2.0, 2.5, 3.0, 3.5, 4.0, 4.5, 5.0, 5.5, 6.0, 6.5, 7.0, 7.5, 8.0, 8.5, 9.0 or 9.5 mg per product calculated as nicotine in the form of nicotine base.

9. The product according to claim 1, wherein said chewing gum composition consists of particles being free from nicotine selected from the group consisting of tobacco, nicotine salts, nicotine base, stabilized nicotine, and mixtures thereof.

10. The product according to claim 1, wherein said product comprises at least one additive selected from the group consisting of a pH adjusting agent, a filler, a sweetener or a flavor.

11. The product according to claim 10, wherein said pH adjusting agent is selected from the group consisting of carbonates acetates, glycinates, gluconates, borates, glycerophosphates or citrates of alkaline metals or ammonium, phosphate systems.

12. The product according to claim 11, wherein said pH adjusting agent is sodium bicarbonate or sodium carbonate, and mixtures thereof.

13. The product according to claim 11, wherein said pH adjusting agent is encapsulated or embedded which physically separates the pH adjusting agent from the nicotine selected from the group consisting of tobacco, nicotine salts, nicotine base, stabilized nicotine, and mixtures thereof.

14. The product according to claim 10, wherein said filler is selected from the group consisting of polysaccharides, polyols, sugars, natural fibers, microcrystalline cellulose, cellulose and cellulose derivatives, and mixtures thereof.

15. The product according to claim 10, wherein said sweetener is selected from the group consisting of mono-di-tri- and polysaccharides, polyols such as sucrose, glucose, dextrose, maltose, fructose, saccharin, aspartame, acesulfame, sucralose, saccharin and cyclamates, and mixtures thereof.

16. The product according to claim 10, wherein said flavor is selected from the group consisting of bergamot, *eucalyptus*, orange, mandarin, citrus, lemon, peppermint, mint, menthol, liquorice, wintergreen, tobacco, coffee, vanilla, lime, apple, peach, and mixtures thereof.

17. The product according to claim 1, wherein said pouch is manufactured from material selected from the group consisting of pharmaceutically acceptable membrane materials.

18. The product according to claim 1, wherein said product comprises from 50 mg to 2000 mg of said powder.

19. The product according to claim 18, wherein said product comprises 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900 or 1950 mg of said powder.

20. The nicotine oral delivery product of claim 1, further comprising a suitable granulating agent.

21. The nicotine oral delivery product of claim 20, wherein the a suitable granulating agent is selected from the group consisting of polyvinylpyrrolidone and anionic copolymers based on methacrylic acid and methyl methacrylate.

* * * * *